(12) United States Patent
Kinooka et al.

(10) Patent No.: US 9,822,344 B2
(45) Date of Patent: Nov. 21, 2017

(54) METHOD FOR CULTURING PLURIPOTENT STEM CELLS

(71) Applicant: OSAKA UNIVERSITY, Osaka (JP)

(72) Inventors: Masahiro Kinooka, Osaka (JP); Meehae Kim, Osaka (JP); Yukako Fujinaga, Osaka (JP); Yo Sugawara, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 14/655,804

(22) PCT Filed: Dec. 26, 2013

(86) PCT No.: PCT/JP2013/084932
§ 371 (c)(1),
(2) Date: Jun. 26, 2015

(87) PCT Pub. No.: WO2014/104207
PCT Pub. Date: Jul. 3, 2014

(65) Prior Publication Data
US 2015/0329831 A1    Nov. 19, 2015

(30) Foreign Application Priority Data

Dec. 28, 2012 (JP) ................................ 2012-288783

(51) Int. Cl.
*C12N 5/074* (2010.01)

(52) U.S. Cl.
CPC ........ *C12N 5/0696* (2013.01); *C12N 2501/58* (2013.01); *C12N 2501/734* (2013.01); *C12N 2501/998* (2013.01)

(58) Field of Classification Search
None
See application file for complete search history.

(56) References Cited

U.S. PATENT DOCUMENTS

| 2009/0202431 | A1* | 8/2009 | Gibbs, Jr. | .......... | A61K 39/0011 424/1.49 |
| 2010/0197014 | A1* | 8/2010 | Agulnick | ............. | C12N 5/0603 435/366 |
| 2012/0058554 | A1* | 3/2012 | Deshayes | ............. | C12N 5/0075 435/354 |
| 2012/0164729 | A1  | 6/2012 | Tomizawa |

FOREIGN PATENT DOCUMENTS

| JP | 2012-143229 A | 8/2012 |
| WO | 2009/041984 A1 | 4/2009 |
| WO | 2014/072720 A2 | 5/2014 |

OTHER PUBLICATIONS

Wesseling et al. "A mechanism for inhibition of E-cadherin-mediated cell-cell adhesion by the membrane-associated mucin episialin/MUC1", Molecular Biology of the Cell 7(4): 565-577, 1996.*
Anderson et al. "Rho and Rho-kinase (ROCK) signaling in adherens and gap junction assembly in corneal epithelium." Investigative ophthalmology & visual science 43(4): 978-986, 2002.*
Sugawara et al. "Botulinum hemagglutinin disrupts the intercellular epithelial barrier by directly binding E-cadherin." The Journal of Cell Biology 189(4): 691-700, 2010.*
Kim et al., "Cardiomyogenic induction of human mesenchymal stem cells by altered Rho family GTPase expression of dendrimer-immobilized surface with D-glucose display," Biomaterials, 31: 7666-7677 (2010).
Mashayekhan et al., "Enrichment of undifferentiated mouse embryonic stem cells on a culture surface with a glucose-displaying dendrimer," Biomaterials, 29: 4236-4243 (2008).
Ohno et al., "Analysis of morphology and E-cadherin expression of embryoid body organized from ES cells," Japanese Journal of Medical Technology, 56: 1221-1226 (2007) (see English abstract).
Hawkins et al., "E-Cadherin and, in Its Absence, N-cadherin Promotes Nanog Expression in Mouse Embryonic Stem Cells via STAT3 Phosphorylation," Stem Cells, 30: 1842-1851 (2012).
Sugawara et al., "Botulinum Hemagglutinin Distrupts E-Cadherin-Mediated Cell to Cell Adhesion and the Epithelial Intercellular Barrier," Japanese Journal of Bacteriology, 66: 322 (2011).
Kim et al., "Maintenance of undifferentiated state of human induced pluripotent stem cells on dendrimer-immobilized culture surface," Journal of Japanese Society for Biomaterials, 31: 154-157 (2013) (see English abstract).
Kim et al., "Kinetic Analysis of Deviation From the Undifferentiated State in Colonies of Human Induced Pluripotent Stem Cells on Feeder Layers," Biotechnology and Bioengineering [online], 111: 1128-1138 (2014).
International Search Report issued in corresponding International Patent Application No. PCT/JP2013/084932 dated Mar. 25, 2014.
Extended European Search Report issued in corresponding European Patent Application No. 13868965.8 dated Apr. 26, 2016.
Soncin et al., "Abrogation of E-Cadherin-Mediated Cell-Cell Contact in Mouse Embryonic Stem Cells Results in Reversible LIF-Independent Self-Renewal," Stem Cells, 27: 2069-2080 (2009).

(Continued)

*Primary Examiner* — Emily Cordas
(74) *Attorney, Agent, or Firm* — Morgan, Lewis & Bockius LLP

(57) ABSTRACT

Provided is a method by which cells deviated from the undifferentiated state, which emerge in a colony during culture of stem cells having pluripotency, can be removed. In one aspect, provided is a method for culturing stem cells having pluripotency, the method including performing cell culture in the presence of a substance that can inhibit cell-cell adhesion. In another aspect, provided is a method for removing cells deviated from the undifferentiated state, the cells being cells that have emerged or may possibly emerge during culture of stem cells having pluripotency, the method including performing cell culture in the presence of a substance that can inhibit cell-cell adhesion. In still another aspect, provided is a method for maintaining the undifferentiated state of stem cells having pluripotency, the method including performing cell culture in the presence of a substance that can inhibit cell-cell adhesion.

17 Claims, 13 Drawing Sheets

(56) References Cited

OTHER PUBLICATIONS

Mohamet et al., "Abrogation of E-Cadherin-Mediated Cellular Aggregation Allows Proliferation of Pluripotent Mouse Embryonic Stem Cells in Shake Flask Bioreactors," PLOS One, 5: e12921 (2010).

Lee et al., "Production of anti-neurotoxin antibody is enhanced by two subcomponents, HA1 and HA3b, of Clostridium botulinum type B 16S toxin-haemagglutinin," Microbiology, 151: 3739-3747 (2005).

Jin et al., "Disruption of the epithelial barrier by botulinum haemagglutinin (HA) proteins—differences in cell tropism and the mechanism of action between HA proteins of types A or B, and HA proteins of type C," Microbiology, 155: 35-45 (2009).

\* cited by examiner

METHOD FOR CULTURING PLURIPOTENT STEM CELLS

TECHNICAL FIELD

The present disclosure relates to a method for culturing stem cells having pluripotency, a method for removing cells deviated from the undifferentiated state, the cells being cells that have emerged or may possibly emerge during culture of stem cells having pluripotency, a method for maintaining an undifferentiated state of stem cells having pluripotency, a composition to be used for these methods, and a kit to be used for these methods.

BACKGROUND ART

In mass culture of pluripotent stem cells such as human iPS (induced pluripotent stem) cells, a series of amplification culture (subculture) processes are repeated so that many undifferentiated cells are prepared. It is known that in this series of culture processes, cells deviated from the undifferentiated state, that is, "deviated cells", spontaneously emerge.

It is known that the deviated cells have a division potential that is nearly equivalent to that of undifferentiated cells, and induce the conversion from undifferentiated cells to deviated cells. In other words, when deviated cells emerge, the proliferation rate thereof exceeds that of undifferentiated cells, and the proliferation of undifferentiated cells is suppressed.

The emergence of deviated cells is frequently observed in culturing operations performed by unskilled culture operators. Further, an excessively large colony size and fusion of colonies are known to be factors of the emergence. Therefore, subculture at low confluence, and maintenance of uniformity at seeding, make it possible to decrease the frequency of appearance of deviated cells to some extent. Further, by using a medium developed in recent years, the frequency of appearance of deviated cells is suppressed to some extent. Deviated cells, however, still spontaneously emerge, and in the case where the cells emerge, it is still essential to remove colonies that contain deviated cells.

In order to maintain the undifferentiated state, colonies containing deviated cells are carefully removed by pipetting operations under a microscope apparatus upon subculture. A device performing such an operation of removing colonies, for example, an observing device combined with pipetting by robot handling, has been developed as well.

Further, Patent Document 1 discloses culture of pluripotent stem cells in the presence of activin for proliferating pluripotent stem cells such as iPS cells while maintaining undifferentiated states thereof.

PRIOR ART DOCUMENT

Patent Document

[Patent Document 1] JP2012-143229A

SUMMARY OF THE INVENTION

Problem to be Solved by the Invention

As described above, a deviation phenomenon tends to occur in subculture of pluripotent stem cells such as human iPS cells, and to maintaining the undifferentiated state is difficult. After several times of subculture, it is likely that the deviation phenomenon occurs in many iPS cell colonies and the colonies can become inferior colonies that contain cells deviated from the undifferentiated state. Complicated operations such as careful culturing and careful colony sorting are therefore indispensable. From the viewpoint of promoting the stem cell industry as well, a method for maintaining undifferentiated states of pluripotent stem cells, that involves less complicated operations and can be performed by a non-expert, has been desired.

The present disclosure, in one aspect, provides a method by which "a cell deviated from the undifferentiated state", which emerges in a colony during culture of a stem cell having pluripotency, can be removed.

Means for Solving the Problem

The present disclosure, in one aspect, relates to a method for culturing a stem cell having pluripotency, the method including performing cell culture in the presence of a substance that can inhibit cell-cell adhesion. The present disclosure, in another aspect, relates to a method for removing a cell deviated from the undifferentiated state, the cell being a cell that has emerged or may possibly emerge during culture of a stem cell having pluripotency, the method including performing cell culture in the presence of a substance that can inhibit cell-cell adhesion. The present disclosure, in still another aspect, relates to a method for maintaining an undifferentiated state of a stem cell having pluripotency, the method including performing cell culture in the presence of a substance that can inhibit cell-cell adhesion. The present disclosure, in still another aspect, relates to a composition containing a substance that can inhibit cell-cell adhesion, for use in the above-described method according to the present disclosure. The present disclosure, in still another aspect, relates to a kit including a medium component for a stem cell having pluripotency, and a substance that can inhibit cell-cell adhesion.

Effect of the Invention

According to present disclosure, in one aspect, it is possible to achieve an effect that "a cell deviated from the undifferentiated state", which emerges in a colony during culture of a stem cell having pluripotency, can be removed.

DESCRIPTION OF PREFERRED EMBODIMENTS

Figure 1:
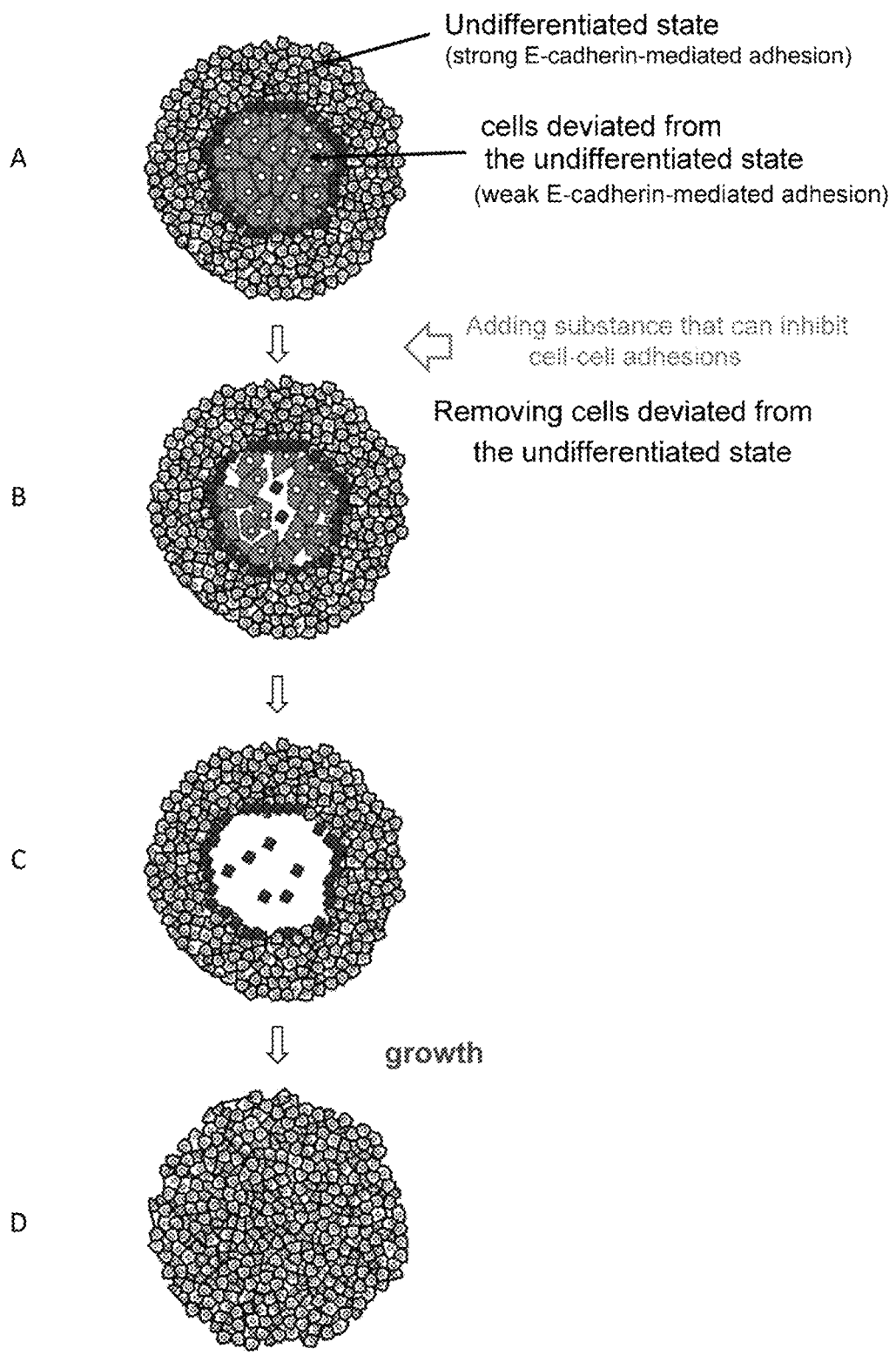
FIG. 1 explains how "cells deviated from the undifferentiated state", which have emerged in a colony during culture of stem cells having pluripotency, are removed by addition of a substance that can inhibit cell-cell adhesion, in one embodiment of the present disclosure.

The present disclosure, in one aspect, is based on knowledge that in the case where stem cells having pluripotency are cultured in the presence of a substance that can inhibit cell-cell adhesion, cells deviated from the undifferentiated state, which have emerged and/or emerge in colonies under culture, can be removed. Further, the present disclosure, in one aspect, is based on knowledge that in the case where undifferentiated cells and deviated cells are mixed in cultured cells, a substance that can inhibit cell-cell adhesion can selectively remove the cells deviated from the undifferentiated state In present disclosure, one or more non-limiting embodiments in which the addition of a substance that can inhibit cell-cell adhesion enables removal of "cells deviated from the undifferentiated state" that grew in colonies during culture of stem cells having pluripotency are described based on FIG. 1. A of FIG. 1 illustrates a state in which cells deviated from the undifferentiated state have emerged in a center part of a colony of cells in an undifferentiated state cultured on a plate. In this situation, when a "substance that can inhibit cell-cell adhesion" is added to a culture solution, the cells deviated from the undifferentiated state start being removed (B of FIG. 1), and soon deviated cells disappear in the center part of the colony (C of FIG. 1). Thereafter, the culture is continued, whereby cells in the undifferentiated state proliferate, and a colony in the undifferentiated state is formed (D of FIG. 1). As illustrated in this drawing, according to the present disclosure, in one or more non-limiting embodiments, "cells deviated from the undifferentiated state" can be removed as if "being erased with an eraser".

Figure 2:
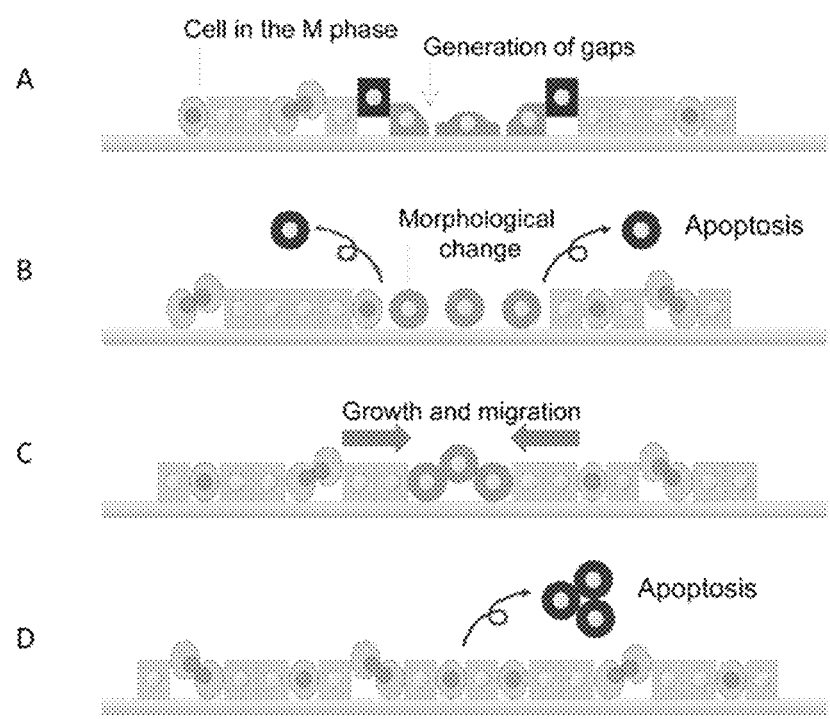
FIG. 2 explains how "cell deviated from the undifferentiated state", which have emerged in a colony during culture of stem cells having pluripotency, are removed by addition of a substance that can inhibit cell-cell adhesion, in one embodiment of the present disclosure.

The mechanism with which cells deviated from the undifferentiated state are removed in the embodiment illustrated in FIG. 1 can be estimated as described below, though the present disclosure does not have to be interpreted exclusively with this mechanism. First, cells having deviated from the undifferentiated state have weaker cell-cell adhesion and adhesion to substrate, as compared with cells in the undifferentiated state, and it can be considered that gaps tend to be formed between cells (A of FIG. 2). Then, the following can be considered: a substance that can inhibit cell-cell adhesion enters the gaps between cells, which causes the cells deviated from the undifferentiated state to have further weaker cell-cell adhesion, and this causes morphological change to occur, thereby suppressing cell proliferation (B of FIG. 2). Further, the following can be considered: here, cells deviated from the undifferentiated state, which have weaker cell adhesion on substrates, float and are removed by apoptosis (B of FIG. 2). As cells in the undifferentiated state therearound are proliferating, deviated cells are pressed and enclosed in the center part (C of FIG. 2), and eventually are removed by apoptosis (D of FIG. 2).

Figure 3:
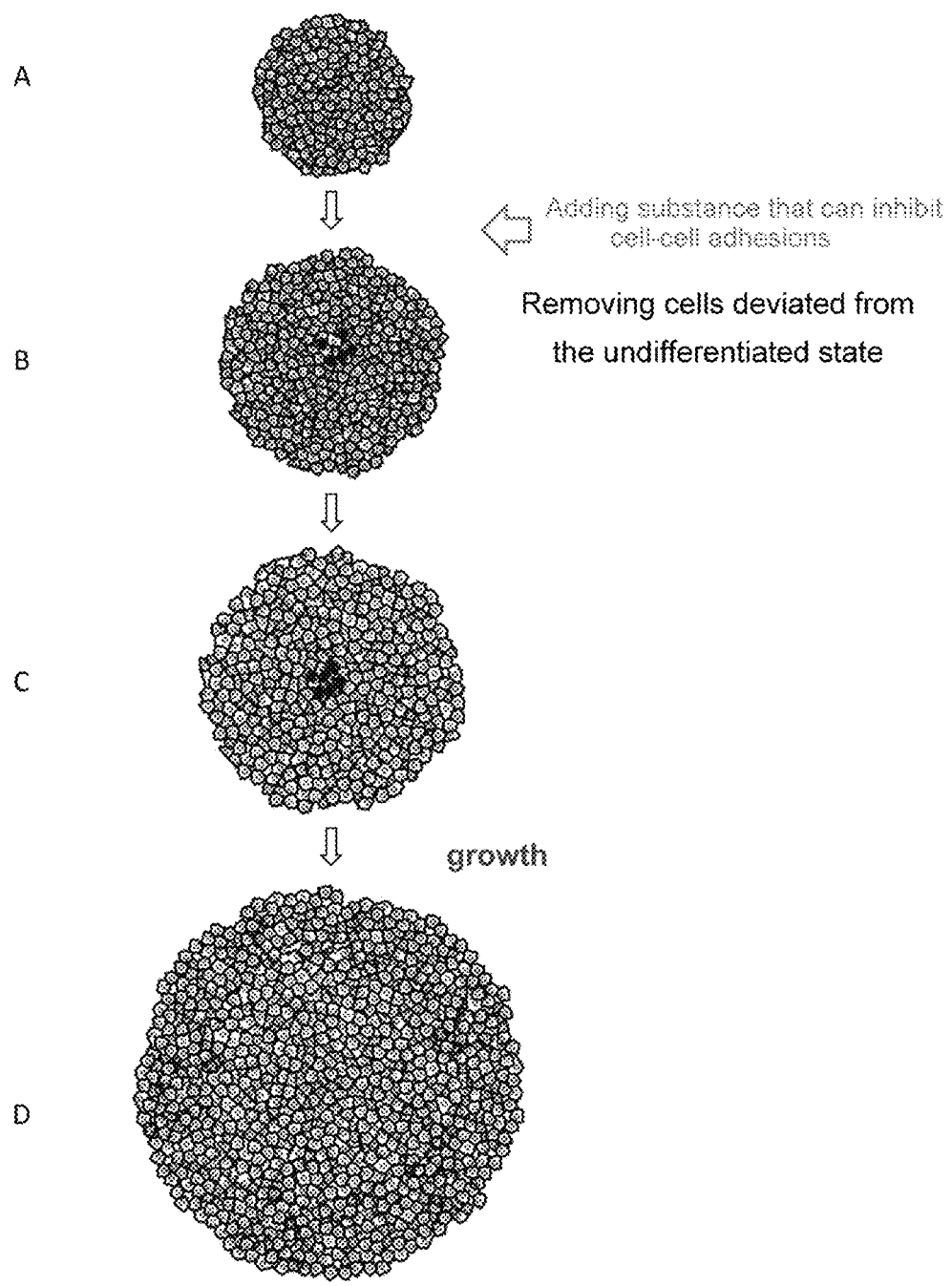
FIG. 3 explains how "cell deviated from the undifferentiated state", which emerge in a colony during culture of stem cells having pluripotency, are removed by addition of a substance that can inhibit cell-cell adhesion, in one embodiment of the present disclosure.

In the present disclosure one or more non-limiting embodiments in which the addition of a substance that can inhibit cell-cell adhesion enables removal of "cells deviated from the undifferentiated state" that emerge in colonies during culture of stem cells having pluripotency are described based on FIG. 3. A of FIG. 3 illustrates a colony of cells in the undifferentiated state cultured on a plate. In this situation, when a "substance that can inhibit cell-cell adhesion" is added to a culture medium, even if cells deviated from the undifferentiated state emerge in this colony (B of FIG. 3), the proliferation of deviated cells is suppressed, and eventually such cells are removed (C of FIG. 3). Thereafter, as culture is continued, colonies in the undifferentiated state are continuously formed (D of FIG. 3).

Figure 4:
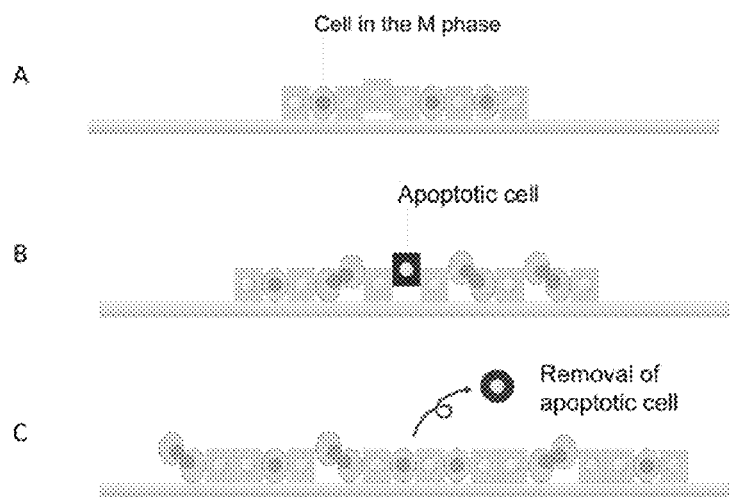
FIG. 4 explains how "cell deviated from the undifferentiated state", which emerge in a colony during culture of stem cells having pluripotency, are removed by addition of a substance that can inhibit cell-cell adhesion, in one embodiment of the present disclosure.

The mechanism with which cells deviated from the undifferentiated state are removed in the embodiment illustrated in FIG. 3 can be estimated as described below, though the present disclosure does not have to be interpreted exclusively with this mechanism. It can be considered that first, the colony is a colony of cells in the undifferentiated state, and they have strong mutual cell-cell adhesion (A of FIG. 4). Spontaneously cells deviated from the undifferentiated state emerge in this colony (B of FIG. 4). It can be considered that cells deviated from the undifferentiated state have weaker cell-cell adhesion as compared with cells in the undifferentiated state, and gaps tend to be formed between the cells. It can be considered that a substance that can inhibit cell-cell adhesion enters the gaps between cells, which causes the cells deviated from the undifferentiated state to have further weaker cell-cell adhesion, and this causes morphological change to occur, thereby suppressing cell proliferation. Further, the following can be considered: here, cells deviated from the undifferentiated state, which have no cell adhesion with culture surfaces, are pressed out by cells in the undifferentiated state therearound that are continuously proliferating, and are removed by apoptosis (C of FIG. 4).

The present disclosure, therefore, in one aspect, relates to a method for culturing stem cells having pluripotency, the method including performing cell culture in the presence of a substance that can inhibit cell-cell adhesion (hereinafter also referred to as "the culturing method according to the present disclosure"). By the culturing method according to the present disclosure, in one aspect, an effect is achieved that "cells deviated from the undifferentiated state", which emerge in a colony during culture of stem cells having pluripotency, can be removed.

The present disclosure, therefore, in another aspect, relates to a method for removing cells deviated from the undifferentiated state, the cells being cells that have emerged or may possibly emerge during culture of stem cells having pluripotency, the method including performing cell culture in the presence of a substance that can inhibit cell-cell adhesion (hereinafter also referred to as "the removing method according to the present disclosure"). By the culturing method according to the present disclosure, and/or, the removing method according to the present disclosure, in one aspect, cells deviated from the undifferentiated state can be removed from a colony of cells in the undifferentiated state in which deviated cells emerge and that therefore deteriorates, whereby a colony of cells in the undifferentiated state or a colony composed of cells in the undifferentiated state can be obtained.

The present disclosure, therefore, in another aspect, relates to a method for forming a colony composed of cells in the undifferentiated state out of a colony where cells deviated from the undifferentiated state emerge and that therefore deteriorates, the method including culturing the deteriorated colony in the presence of a substance that can inhibit cell-cell adhesion (hereinafter also referred to as "the colony forming method according to the present disclosure").

Further, by the culturing method according to the present disclosure and/or the removing method according to the present disclosure, in one aspect, it is possible to culture cells in the undifferentiated state or cells in the undifferentiated state exclusively. The present disclosure, therefore, in another aspect, relates to a method for maintaining the undifferentiated state of stem cells having pluripotency, the method including performing cell culture in the presence of a substance that can inhibit cell-cell adhesion (hereinafter also referred to as "the maintaining method according to the present disclosure").

[Stem Cells Having Pluripotency]

In the present disclosure, the stem cell having pluripotency is a human pluripotent stem cell, in one or more non-limiting embodiments. In the present disclosure, the human pluripotent stem cell is a human iPS (induced pluripotent stem) cell or a human ES (embryonic stem) cell, in one or more non-limiting embodiments.

[Cells Deviated from the Undifferentiated State]

In the present disclosure, the cells deviated from the undifferentiated state can be distinguished cells in an undifferentiated state, unlike cells whose cell morphology is in an undifferentiated state, in one or more non-limiting embodiments. In the present disclosure, the "cell deviated from the undifferentiated state" is also referred to as a "deviated cell" or a "cell deviated from the undifferentiated state" in some cases. That a cell has become a deviated cell can be confirmed by disappearance of an undifferentiation marker, in one or more non-limiting embodiments. The undifferentiation marker is Oct3/4, Nanog, SSEA-4, or TRA-1-60 in one or more non-limiting embodiments.

[Substance that can Inhibit Cell-Cell Adhesion]

In the present disclosure, the substance that can inhibit cell-cell adhesion is a substance that has an activity of inhibiting E-cadherin function, in one or more non-limiting embodiments. In the present disclosure, from the viewpoint of efficiently removing deviated cells, the substance that can inhibit cell-cell adhesion preferably has an ability to bind to cell surfaces, in addition to the activity of inhibiting E-cadherin function, in one or more non-limiting embodiments. The ability to bind to cell surfaces is an ability to bind to cell surfaces of stem cells having pluripotency, in one or more non-limiting embodiments.

(HA)

In the present disclosure, the substance that can inhibit cell-cell adhesion is hemagglutinin (HA) of the neurotoxin complex of *Clostridium botulinum*, in one or more non-limiting embodiments. In the present disclosure, from the viewpoint of efficiently removing deviated cells, the substance that can inhibit cell-cell adhesion is a complex composed of two or three components selected from the group consisting of three hemagglutinin subcomponents HA1 (HA33), HA2 (HA17), and HA3 (HA70) of the neurotoxin complex of *Clostridium botulinum*, or a substance containing the complex, in one or more non-limiting embodiments. Further, from the viewpoint of efficiently removing deviated cells, the substance that can inhibit cell-cell adhesion is a complex composed of HA2 (HA17) and HA3 (HA70), a complex composed of the three components, or a substance containing the complex, in one or more non-limiting embodiments. From the viewpoint of causing the activity of inhibiting E-cadherin function to be expressed, and from the viewpoint of efficiently removing deviated cells, the subcomponent HA3 (HA70) is preferably of *Clostridium botulinum* type A or *Clostridium botulinum* type B, in one or more embodiments. Further, the subcomponents HA1 (HA33) and HA2 (HA17) may be of any one of *Clostridium botulinum* type A, *Clostridium botulinum* type B, and *Clostridium botulinum* type C, in one or more non-limiting embodiments. Regarding HA, each subcomponent may be of a recombinant type or a natural type, in one or more non-limiting embodiments.

[Cell Culture in the Presence of Substance that can Inhibit Cell-Cell Adhesion]

In the present disclosure, "cell culture in the presence of the substance that can inhibit cell-cell adhesion" can use culture conditions, a culture medium, and the like that are conventionally used and/or will be developed in future for stem cells having pluripotency, and this can be achieved by making the substance that can inhibit cell-cell adhesion be present in the medium under the culture conditions. In one or more non-limiting embodiments, the substance that can inhibit cell-cell adhesion may be added to a culture medium under culture, or alternatively, a medium to which the substance that can inhibit cell-cell adhesion is preliminarily added may be used for culture. As the culture medium, the culture plate, and the like, those which are commercially available may be used.

The "substance that can inhibit cell-cell adhesion" may be added to a medium after deviated cells are confirmed, or alternatively, may be added to a medium at a stage where deviated cells have not emerged yet.

The concentration of the "substance that can inhibit cell-cell adhesion" present in a medium is a substantially effective concentration that enables removal of deviated cells, in one or more non-limiting embodiments, and any person skilled in the art is able to set the concentration. From the viewpoint of efficiently removing deviated cells, the concentration of the "substance that can inhibit cell-cell adhesion" present in the medium is 5 nM or more, 10 nM or more, or alternatively, 15 nM or more, for example, in one or more non-limiting embodiments. From the same viewpoint, the concentration is 200 nM or less, 150 nM or less, or alternatively, 100 nM or less.

In one or more non-limiting embodiments in which the "substance that can inhibit cell-cell adhesion" is present in the medium, the administration of the same may be a single administration per one period, which is until next medium exchange, or serial administration, or alternatively, occasional administration.

In the present disclosure, cell culture includes subculture, in one or more non-limiting embodiments. By the culturing method according to the present disclosure, and/or according to the removing method according to the present disclosure, in one aspect, an effect can be achieved that the ratio of an undifferentiated colony (a colony that is formed with undifferentiated cells and that substantially does not contain deviated cells) in a colony formed after subculture can be improved. The subculture can be performed by any of techniques that are conventionally known and are to be developed in future, in one or more non-limiting embodiments.

In the present disclosure, the cell culture may be culture using feeder cells, or may be feeder-free culture, in one or more non-limiting embodiments. Examples of the feeder cells include MEF (Mouse Embryo Fibroblast) cells, SL10, and SNL 76/7 feeder cells, in one or more non-limiting embodiments. Among the feeder cells, feeder cells that allow the migration speed of stem cells having pluripotency to be relatively slow are preferred, in one or more non-limiting embodiments. In one or more non-limiting embodiments, the feeder cells are preferably SNL 76/7 feeder cells, from the viewpoint that the migration of stem cells having pluripotency is relatively slow and a colony of deviated cells is allowed to emerge in the center part of a colony during culture of stem cells having pluripotency.

The cell culture is preferably performed under conditions in which deviated cells may possibly emerge in a center part of a colony during culture of stem cells having pluripotency, from the viewpoint that the deviated cells can be removed efficiently, in one or more non-limiting embodiments. In one or more non-limiting embodiments, the migration of stem cells having pluripotency is inhibited and/or suppressed, whereby deviated cells can efficiently emerge in the center part of the colony.

In another aspect, the present disclosure relates to a method for culturing stem cells having pluripotency, the method including culturing cells in the presence of a substance that can inhibit migration, and performing cell culture in the presence of a substance that can inhibit cell-cell adhesion. By the culturing method according to the present aspect, in one aspect, deviated cells are allowed to emerge in the center part of a colony during culture of stem cells having pluripotency, and this makes it possible to achieve an effect of efficiently removing deviated cells.

The present disclosure, in another aspect, relates to a method for removing deviated cells that have emerged or may possibly emerge during culture of stem cells having pluripotency, the method including culturing cells in the presence of a substance that can inhibit migration, and performing cell culture in the presence of a substance that can inhibit cell-cell adhesion. By the culturing method according to the present aspect, and/or by the removing method according to the present aspect, in one aspect, deviated cells can be removed from a colony of cells in the undifferentiated state in which deviated cells emerge and that therefore deteriorates, whereby a colony of cells in the undifferentiated state or a colony composed of cells in the undifferentiated state can be obtained.

The present disclosure, in another aspect, relates to a method for forming a colony composed of cells in the undifferentiated state out of a colony where deviated cells emerge and that therefore deteriorates, the method including; culturing cells in the presence of a substance that can inhibit migration; and culturing the deteriorated colony in the presence of a substance that can inhibit cell-cell adhesion.

In the present disclosure, in one or more non-limiting embodiments, examples of the substance that can inhibit migration include a substance that suppresses/inhibits activity of a substance relating to migration of stem cells having pluripotency. In the present disclosure, in one or more non-limiting embodiments, examples of the substance that can inhibit migration include a migration inhibitor. In one or more non-limiting embodiments, examples of the substance that can inhibit migration include a Rac-1 inhibitor. In one or more non-limiting embodiments, from the viewpoint of efficiently moving deviated cells to the center part of a colony and efficiently removing the deviated cells, the concentration of the "substance that can inhibit migration" that is caused to be present in the medium is 50 µM or more, 100 µM or more, or alternatively, 150 µM or more. From the same viewpoint, the concentration is 200 µM or less.

In one or more non-limiting embodiments, the substance that can inhibit migration may be added to the medium upon culture start, or may be added when the medium is exchanged. In one or more non-limiting embodiments, the substance that can inhibit migration may be added to the medium at a stage where no deviated cell emerges, or alternatively, may be added to the medium after a deviated cell is confirmed.

By the culturing method according to the present disclosure, and/or by the removing method according to the present disclosure, cell culture is performed in the presence of a substance that can inhibit cell-cell adhesion, whereby, in one aspect, deviated cells can be removed automatically from a colony, with a closed space being maintained. Further, in one aspect, even in the case where an artificial operation and/or confirmation, or a special device such as a robot, is not used, deviated cells can be removed from a colony automatically. Further, by the culturing method according to the present disclosure, and/or by the removing method according to the present disclosure, in one aspect, automatically a colony of cells in the undifferentiated state or a colony composed of cells in the undifferentiated state can be obtained.

By using the culturing method according to the present disclosure, and/or the removing method according to the present disclosure, therefore, a colony of cells in the undifferentiated state or a colony composed of cells in the undifferentiated state can be efficiently obtained by an automatic culture device, and further, cells in the undifferentiated state can be mass-produced efficiently in a simple manner.

The present disclosure, in another aspect, relates to a composition that contains a substance that can inhibit cell-cell adhesion (hereinafter also referred to as "the composition according to the present disclosure"). The "substance that can inhibit cell-cell adhesion" in the composition according to the present disclosure is as mentioned above. The composition according to the present disclosure can be used for the culturing method according to the present disclosure, the removing method according to the present disclosure, the colony forming method according to the present disclosure, and/or the maintaining method according to the present disclosure. The present disclosure, therefore, in another aspect, relates to the use of the "substance that can inhibit cell-cell adhesion" in the culturing method according to the present disclosure, the removing method according to the present disclosure, the colony forming method according to the present disclosure, and/or the maintaining method according to the present disclosure.

The present disclosure, in another aspect, relates to a kit including: a medium component for a stem cell having pluripotency; and a substance that can inhibit cell-cell adhesion (hereinafter also referred to as "the kit according to the present disclosure"). The "substance that can inhibit cell-cell adhesion" in the kit according to the present disclosure is as mentioned above. The kit according to the present disclosure can be used for the culturing method according to the present disclosure, the removing method according to the present disclosure, the colony forming method according to the present disclosure, and/or the maintaining method according to the present disclosure. The medium component for stem cells having pluripotency is not limited particularly, and a medium component that has been conventionally used or that is to be developed in future can be used.

The present disclosure further relates to one or more non-limiting embodiments described below. (1) A method for culturing a stem cell having pluripotency, the method including performing cell culture in the presence of a substance that can inhibit cell-cell adhesion. (2) A method for removing a cell that has deviated from an undifferentiated state, the cell being a cell that has emerged or may possibly emerge during culture of a stem cell having pluripotency, the method including: performing cell culture in the presence of a substance that can inhibit cell-cell adhesion. (3) A method for maintaining an undifferentiated state of a stem cell having pluripotency, the method including: performing cell culture in the presence of a substance that can inhibit cell-cell adhesion. (4) The method according to any one of (1) to (3), wherein the stem cell having pluripotency is a human pluripotent stem cell. (5) The method according to (4), wherein the human pluripotent stem cell is either a human iPS cell or a human ES cell. (6) The method according to any one of (1) to (5), wherein the substance that can inhibit cell-cell adhesion is a substance having an activity of inhibiting E-cadherin function. (7) The method according to (6), wherein the substance that can inhibit cell-cell adhesion further has an ability to bind to a cell surface. (8) The method according to any one of (1) to (7), wherein the substance that can inhibit cell-cell adhesion is hemagglutinin (HA) of a neurotoxin complex of *Clostridium botulinum*. (9) The method according to any one of (1) to (8), wherein the substance that can inhibit cell-cell adhesion is a complex composed of two or three components selected from the group consisting of three hemagglutinin subcomponents HAL HA2, and HA3 of the neurotoxin complex of *Clostridium botulinum*. (10) The method according to (9), wherein the subcomponent HA3 of the complex is of *Clostridium botulinum* type A or *Clostridium botulinum* type B. (11) The method according to any one of (1) to (10), wherein the culture is subculture. (12) A composition for culture of a stem cell having pluripotency, the composition containing a substance that can inhibit cell-cell adhesion. (13) A composition for removing a cell deviated from the undifferentiated state, the cell being a cell that has emerged or may possibly emerge during culture of a stem cell having pluripotency, the composition containing a substance that can inhibit cell-cell adhesion. (14) A composition for maintaining an undifferentiated state of a stem cell having pluripotency, the composition containing a substance that can inhibit cell-cell adhesion. (15) The composition according to any one of (12) to (14), wherein the stem cell having pluripotency is a human pluripotent stem cell. (16) The composition according to (15), wherein the human pluripotent stem cell is either a human iPS cell or a human ES cell. (17) The composition according to any one of (12) to (16), wherein the substance that can inhibit cell-cell adhesion is a substance having an activity of inhibiting E-cadherin function. (18) The composition according to (17), wherein the substance that can inhibit cell-cell adhesion further has an ability to bind to a cell surface. (19) The composition according to any one of (12) to (18), wherein the substance that can inhibit cell-cell adhesion is hemagglutinin of a neurotoxin complex of *Clostridium botulinum*. (20) The composition according to any one of (12) to (19), wherein the substance that can inhibit cell-cell adhesion is a complex composed of two or three components selected from the group consisting of three hemagglutinin subcomponents HA1, HA2, and HA3 of the neurotoxin complex of *Clostridium botulinum*. (21) The composition according to (20), wherein the subcomponent HA3 of the complex is of *Clostridium botulinum* type A or *Clostridium botulinum* type B. (22) The composition according to any one of (12) to (21), wherein the culture is subculture. (23) The composition according to any one of (12) to (22), for the method according to any one of (1) to (11). (24) A kit including: a medium component for a stem cell having pluripotency; and a substance that can inhibit cell-cell adhesion. (25) The kit according to (24) for removing a cell that has deviated from an undifferentiated state, the cell being a cell that has emerged or may possibly emerge during culture of a stem cell having pluripotency. (26) The kit according to (24) for culturing a stem cell having pluripotency. (27) The kit according to (24) for removing a cell that has deviated from an undifferentiated state, the cell being a cell that has emerged or may possibly emerge during culture of a stem cell having pluripotency, the composition containing a substance that can inhibit cell-cell adhesion. (28) The kit according to any one of (24) to (27), wherein the stem cell having pluripotency is a human pluripotent stem cell. (29) The kit according to (28), wherein the human pluripotent stem cell is either a human iPS cell or a human ES cell. (30) The kit according to any one of (24) to (29), wherein the substance that can inhibit cell-cell adhesion is a substance having an activity of inhibiting E-cadherin function. (31) The kit according to (30), wherein the substance that can inhibit cell-cell adhesion further has an ability to bind to a cell surface. (32) The kit according to any one of (24) to (31), wherein the substance that can inhibit cell-cell adhesion is hemagglutinin of a neurotoxin complex of *Clostridium botulinum*. (33) The kit according to any one of (24) to (32), wherein the substance that can inhibit cell-cell adhesion is a complex composed of two or three components selected from the group consisting of three hemagglutinin subcomponents HA1, HA2, and HA3 of the neurotoxin complex of *Clostridium botulinum*. (34) The kit according to (33), wherein the subcomponent HA3 of the complex is of Clostridium botulinum type A or Clostridium botulinum type B. (35) The kit according to any one of (24) to (34), wherein the culture is subculture. (36) The kit according to any one of (24) to (35), for the method according to any one of (1) to (11). (37) Use of a substance that can inhibit cell-cell adhesion, in the method according to any one of (1) to (11).

EXAMPLES

Hereinafter, the present disclosure is described in further details by way of examples, though these are examples and the present disclosure is not limited by these examples at all.
[Influences of Hemagglutinin (HA) on iPS Cells (Part 1)]

Figure 5:
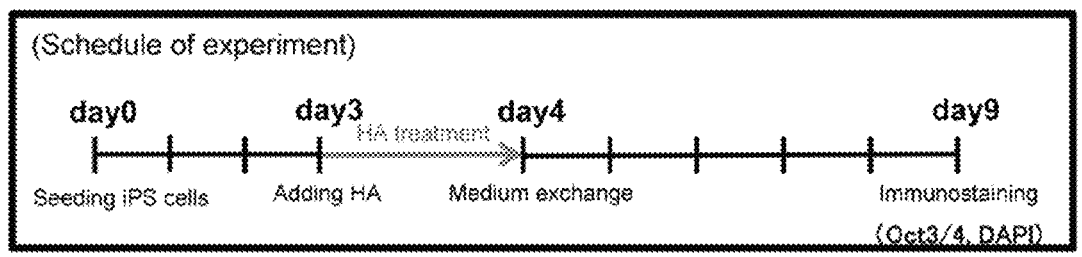
FIG. 5 explains a schedule of an experiment performed in Example.

According to the experiment schedule illustrated in FIG. 5, iPS cells were cultured. First, iPS cells were seeded on feeder cells (day 0), and the culture medium was exchanged with a maintenance medium every 24 hours. At three days after the start (day 3), HA was added, and incubation was carried out for 24 hours. After washed with phosphate buffered saline (PBS) twice, the culture medium was exchanged with maintenance medium (day 4). Thereafter, until nine days after the start (day 9), the culture medium was exchanged with a maintenance medium every 24 hours. After the culture, the expression of Oct3/4 of the cultured cells was confirmed by immunocytostaining, and further, DAPI staining was performed. The used cells, media, and HA, as well as the culture conditions are as follows.
(Cell)
iPS cells: Tic (Np 39)
Feeder cells: SNL 76/7 (Np 5) treated with mitomycin C
(Medium)
iPS cells: Repro Stem (trade name, manufactured by Repro-CELL J, Inc.), 5 ng/mL FGF-2
Feeder cells: DMEM (7% FBS, 1% Penicillin-streptomycin solution)
(Container)
24-well plate (bottom area: 1.9 $cm^2$/well, medium amount: 0.4 mL/well)
(HA)
As HA complex samples, hemagglutinins HA-1 to HA-4 shown in Table 1 below were used, which are Clostridium botulinum neurotoxin complex samples It should be noted that HA-1 and HA-2 are complexes in each of which all of the subcomponents HA1 to HA3 are of the type B, and are HA complex samples that were prepared individually. HA-3 is a HA complex specimen in which HA1 is of the type C and HA2 and HA3 are of the type B. HA-4 is a HA complex specimen in which HA1 and HA2 are of the type B and HA3 is of the type C.

TABLE 1

| HA | HA1 (HA33) | HA2 (HA17) | HA3 (HA70) | E-cadherin inhibiting ability |
|---|---|---|---|---|
| 1 | Type B | Type B | Type B | + |
| 2 | Type B | Type B | Type B | + |
| 3 | Type C | Type B | Type B | + |
| 4 | Type B | Type B | Type C | − |

(HA Preparing and Adding Method)
Dilution of HA: In order to make PBS included in the same dilution series have the same concentrations, two-stage dilution was performed. First, HA was serially diluted with PBS, and it was further diluted using a medium (Repro Stem). (The final concentrations: 100, 50, 10, 1 nM)

Further, bFGF (final concentration: 5 ng/ml) was added, and the HA thus diluted was added to the iPS cells.
(Culture Conditions)
5% $CO_2$ atmosphere at 37° C.

After the subculture of iPS cells, in the exchange of the culture medium at t=72 h (day 3), HA-1 to HA-4 were added at respective concentrations, which was followed by the culture for 24 hours. Thereafter, in the exchange of the culture medium at t=96 h (day 4), the medium was switched to a HA-free medium, and the culture was continued.
(Observation)

At day 3, day 4, day 5, and day 9, the cultured cells were observed with IN Cell Analyzer 2000 (trade name, manufactured by GE healthcare Bio-Sciences Corp.), and images thereof were acquired. Micrographs obtained in the case where HA-1 was added at 100 nM, 50 nM, 10 nM, and 1 nM are illustrated in FIGS. 6, 7, 8, and 9, respectively.

Figure 6:
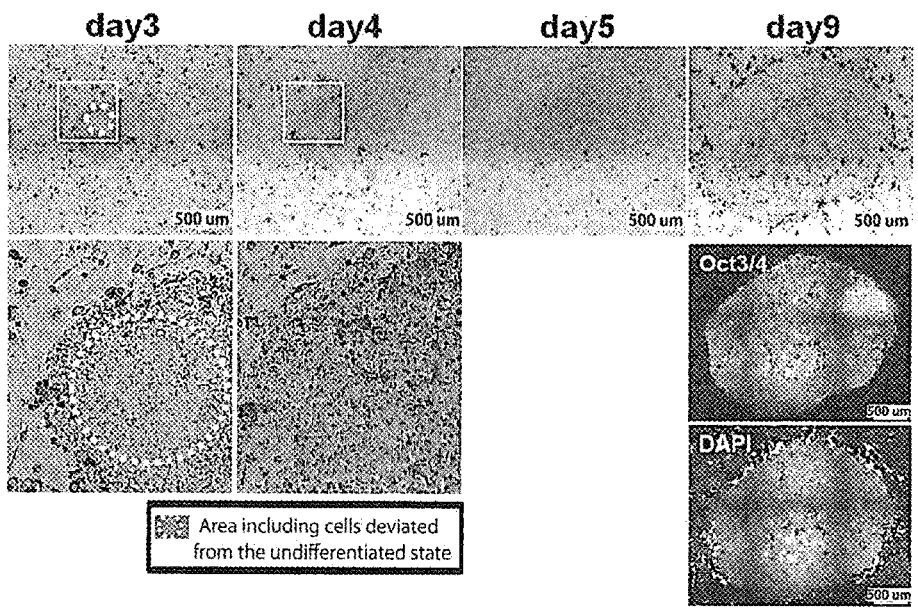
FIG. 6 illustrates exemplary micrographs in the case where HA-1 having a final concentration of 100 nM was added at day 3.

As illustrated in FIG. 6, in the case where HA-1 was added at 100 nM, deviated cells that had emerged as of day 3 were not observed after day 4. At day 4, gaps were formed between cells, and each cell had a slightly elongated shape. After day 5, gaps were filled, each cell had a smaller size, and the cells were densely laid in a form cobblestone-like shape, whereby colonies expanded. At day 9, the areas that included deviated cells that had emerged after day 5 were observed.

Figure 7:
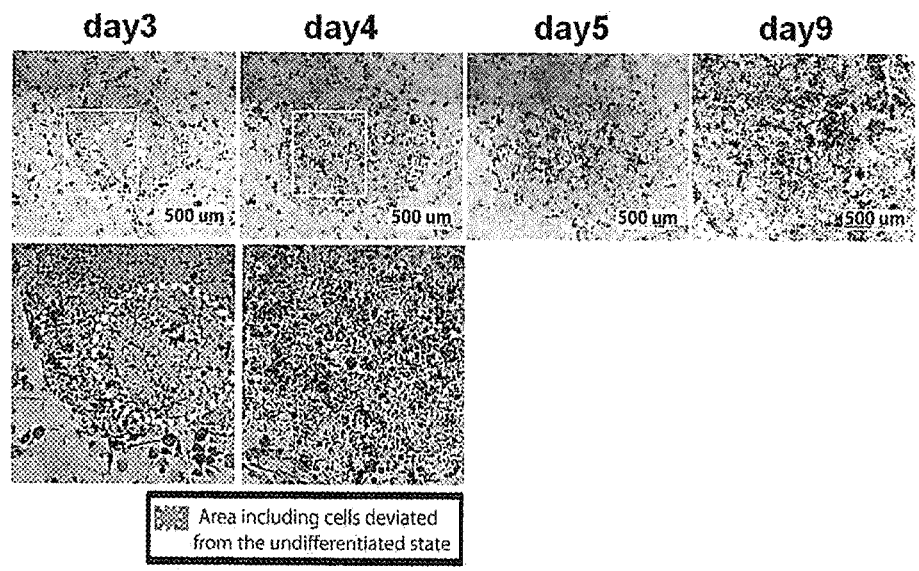
FIG. 7 illustrates exemplary micrographs in the case where HA-1 having a final concentration of 50 nM was added at day 3.

As illustrated in FIG. 7, regarding day 3 to 5, the result of the case where HA-1 was added at 50 nM was identical to the result of the case where HA-1 was added at 100 nM. At day 9, however, no deviated cells were observed.

Figure 8:
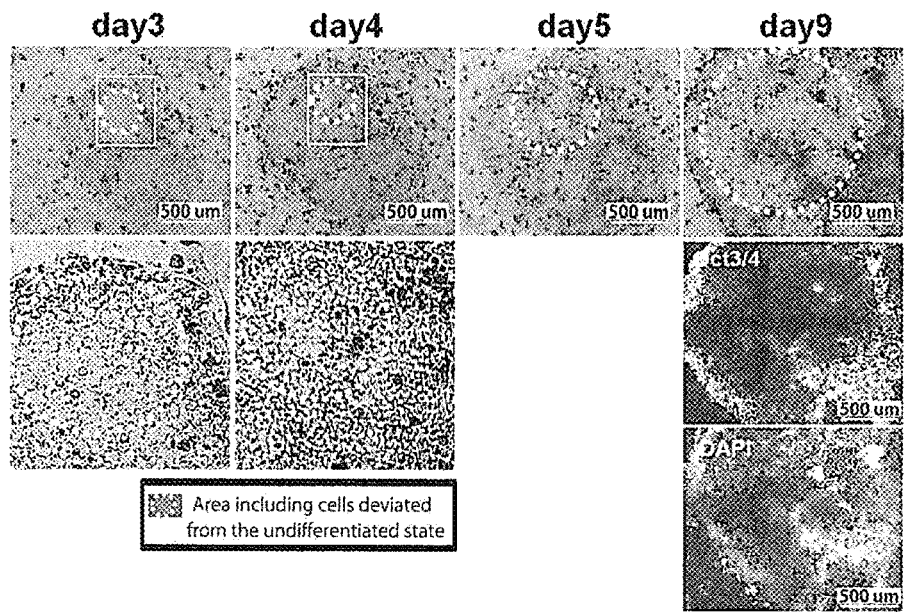
FIG. 8 illustrates exemplary micrographs in the case where HA-1 having a final concentration of 10 nM was added at day 3.

As illustrated in FIG. 8, in the case where HA-1 was added at 10 nM, deviated cells that had emerged as of day 3 appeared to have decreased at day 4. At day 5, however, the areas that included deviated cells were expanded again. Thereafter, the areas that included deviated cells expanded.

Figure 9:
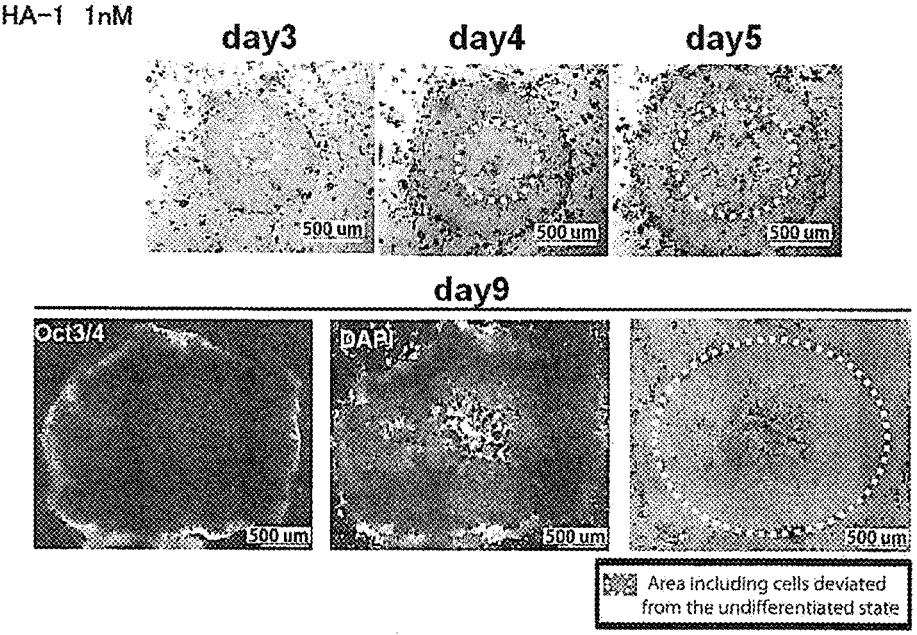
FIG. 9 illustrates exemplary micrographs in the case where HA-1 having a final concentration of 1 nM was added at day 3.

As illustrated in FIG. 9, in the case where HA-1 was added at 1 nM, the areas that included deviated cells that had emerged as of day 3 continuously expanded after day 3. Cell morphology change and decrease of deviated cells were not observed.

Figure 10:
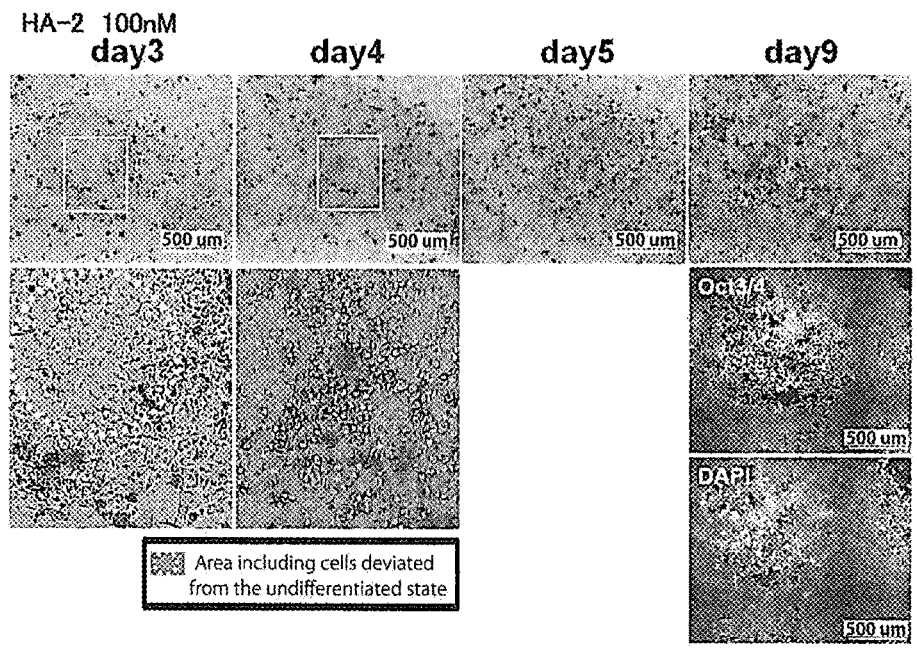
FIG. 10 illustrates exemplary micrographs in the case where HA-2 having a final concentration of 100 nM was added at day 3.
Figure 11:
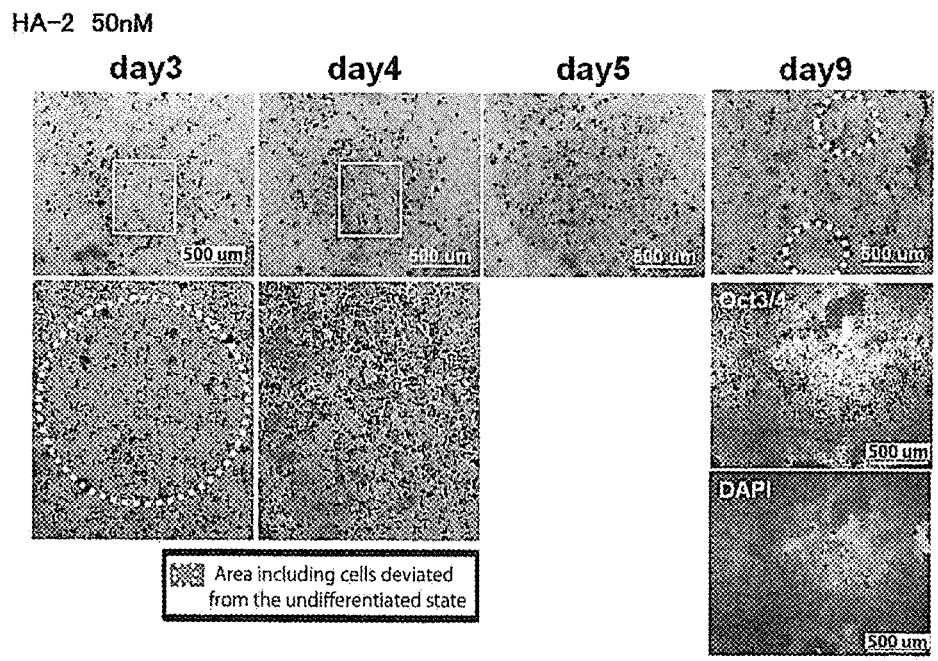
FIG. 11 illustrates exemplary micrographs in the case where HA-2 having a final concentration of 50 nM was added at day 3.
Figure 12:
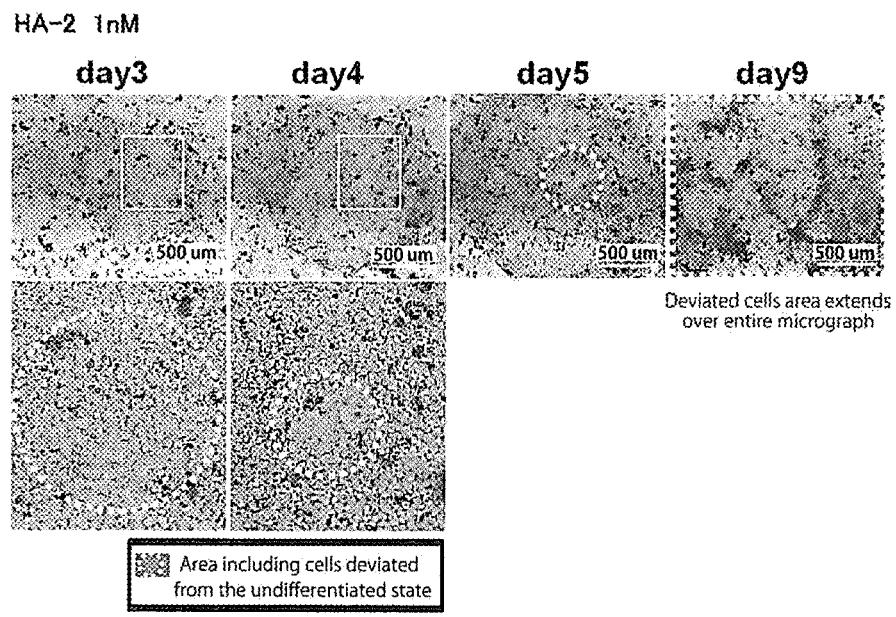
FIG. 12 illustrates exemplary micrographs in the case where HA-2 having a final concentration of 1 nM was added at day 3.

Micrographs obtained in the case where HA-2 was added at 100 nM, 50 nM, and 1 nM are illustrated in FIGS. 10, 11, and 12, respectively. As illustrated in FIG. 10, the result of the case where HA-2 was added at 100 nM was identical to the result of the case where HA-1 was added at 100 nM (FIG. 6). As illustrated in FIG. 11, the result of the case where HA-2 was added at 50 nM was identical to the result of the case where HA-1 was added at 50 nM (FIG. 7). As illustrated in FIG. 12, the result of the case where HA-2 was added at 1 nM was identical to the result of the case where HA-1 was added at 1 nM (FIG. 9).

The results regarding HA-1 and HA-2 are compiled in Table 2 illustrated below. As indicated in Table 2, in the case where HA-1 and HA-2 were added at 100 nM and 50 nM, deviated cells that had emerged as of day 3 shrank and/or disappeared.

Figure 13:
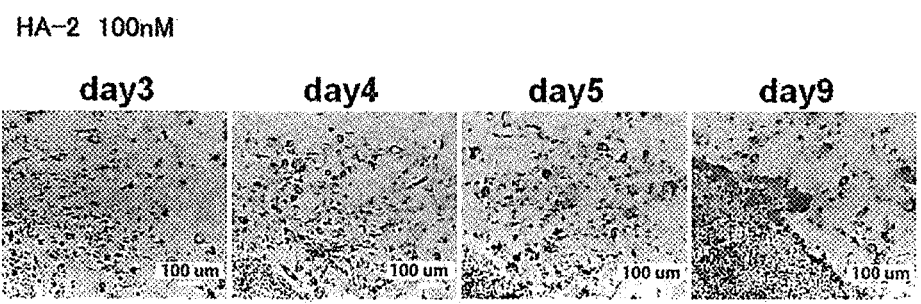
FIG. 13 illustrates exemplary micrographs in the case where HA-2 having a final concentration of 100 nM was added at day 3.

FIG. 13 illustrates results of observation of influences of HA-2 on deviated cells that were brought in during the subculture. As illustrated in this drawing, when HA-2 was added at 100 nM and the cells were treated for 24 hours, deviated cells gradually peeled off.

Figure 14:
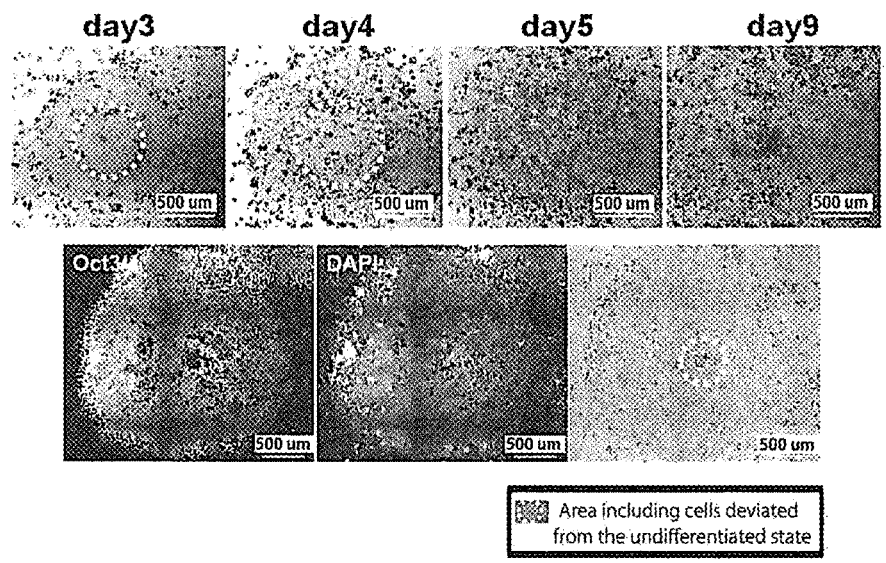
FIG. 14 illustrates exemplary micrographs in the case where HA-3 having a final concentration of 50 nM was added at day 3.
Figure 15:
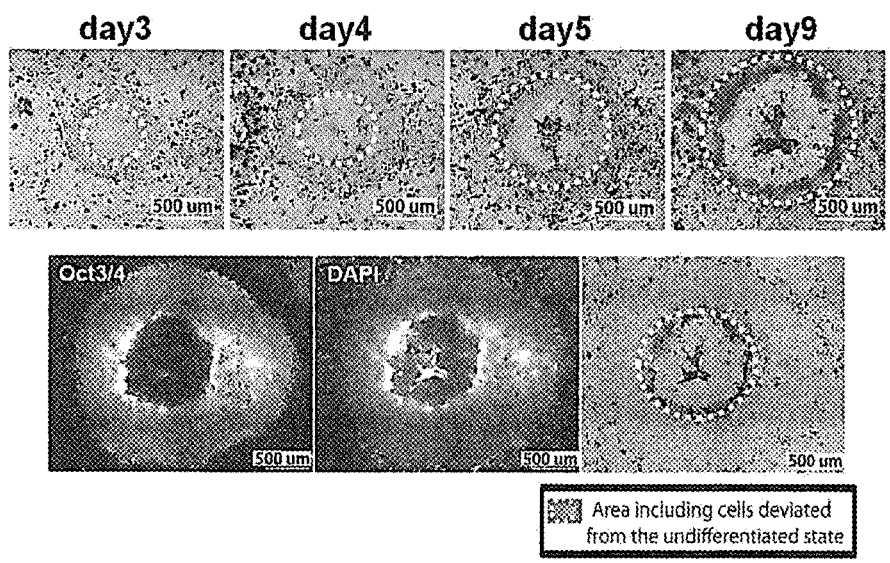
FIG. 15 illustrates exemplary micrographs in the case where HA-3 having a final concentration of 10 nM was added at day 3.

Micrographs obtained in the case where HA-3 was added at 50 nM and 10 nM are illustrated in FIGS. 14 and 15, respectively.

As illustrated in FIG. 14, in the case where HA-3 was added at 50 nM, the areas of deviated cells that had emerged as of day 3 stopped expanding, and after day 4, the areas of deviated cells shrank as deviated cells were proliferated. At day 9, deviated cells remained in a part of the center of the colony. At day 4, gaps were formed between iPS cells, and each iPS cell had a slightly elongated shape. After day 5, as iPS cells were proliferated, colonies formed with iPS cells with cobblestone-like shape densely laid were obtained. On the other hand, feeder cells detach. It should be noted that in the case where HA-3 was added at 100 nM, the same result as that obtained in the case where HA-3 was added at 50 nM was obtained.

As illustrated in FIG. 15, in the case where HA-3 was added at 10 nM, the areas of deviated cells continuously expanded after day 3. Cell morphology form change, decrease of deviated cells, and the detachment of feeder cells were not observed.

Figure 16:
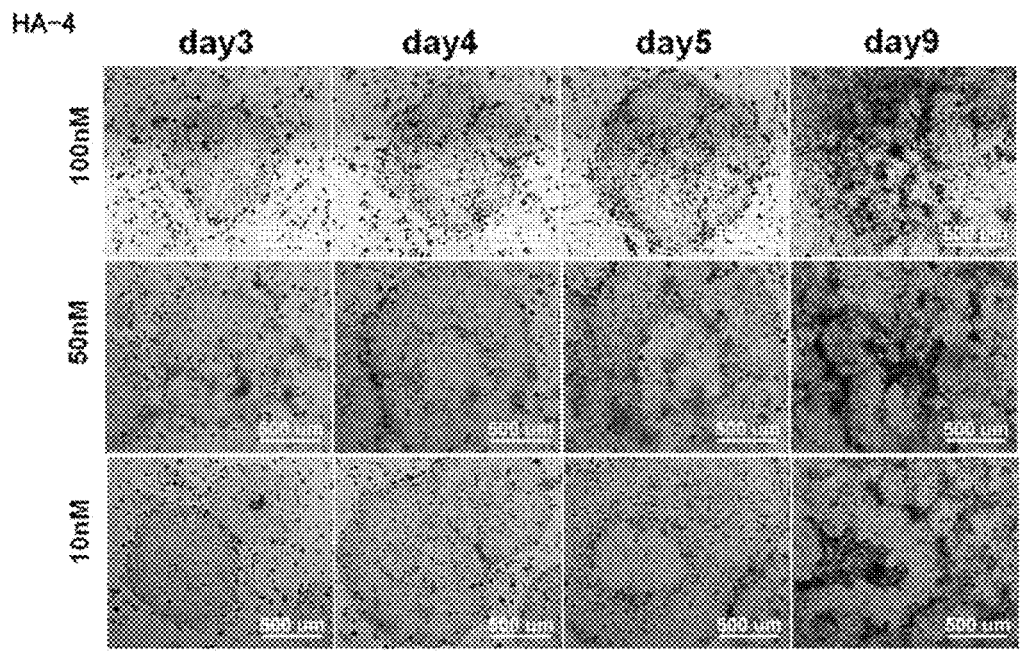
FIG. 16 illustrates exemplary micrographs in the case where HA-4 having final concentrations of 100 nM, 50 nM, and 10 nM was added at day 3.

Micrographs obtained in the case where HA-4 was added at 100 nM, 50 nM, and 10 nM are illustrated in FIG. 16. As illustrated in the drawing, the areas of deviated cells that had emerged as of day 3 continuously expanded. In the case where HA-4 was added at 100 nM, the shrinking of the areas of deviated cells might possibly occur.

The results of the cases of HA-3 and HA-4 are compiled in Table 2 illustrated below.

TABLE 2

| HA | Final concentration | Deviated cell area as of day 3 | Form of colony and iPS cell | Others |
|---|---|---|---|---|
| 1.2 | 100 nM | Disappear | At day 4, slightly elongated cells with gaps there between | Deviated cells brought in upon subculture disappear |
| | 50 nM | | After day 5, cells become dense, thereby forming the shape of normal colonies | |
| | 10 nM | Shrink, and thereafter expand again | No remarkable difference | |
| | 1 nM | Expand | | |
| 3 | 100 nM | Shrink | At day 4, slightly elongated cells with gaps there between | Feeder cells detach |
| | 50 nM | | After day 5, cells become dense, thereby forming shape of normal colonies | |
| | 10 nM | Expand | No remarkable difference | Feeder cells do not detach |
| 4 | 100 nM | Expand | No remarkable difference | |
| | 50 nM | | | |
| | 10 nM | | | |

As illustrated in Table 2, in the cases of HA-1 and HA-2, areas of deviated cells efficiently shrank and/or disappeared, as compared with the cases of HA-3 and HA-4. Further, in the case of HA-3, areas of deviated cells efficiently shrank, and/or the expansion of the areas was efficiently suppressed, as compared with the case of HA-4.

[Influences of Feeder Cells on iPS Cells]

On feeder cells, iPS cells were seeded, and the culture medium was exchanged with a maintenance medium every 24 hours until day 7. After the culture, the expression of Oct3/4 of the cultured cells was confirmed by immunocytostaining, and DAPI staining was performed. The used cells and media, as well as the culture conditions are as follows.

(Cell)
iPS cells: Tic (Np 39)
Feeder cells: MEF
(Medium)
iPS cells: Repro Stem (trade name, manufactured by ReproCELL J, Inc.), 5 ng/mL FGF-2
Feeder cells: DMEM (7% FBS, 1% Penicillin-streptomycin solution)
(Container)
24-well plate (bottom area: 1.9 cm$^2$/well, medium amount: 0.4 mL/well)
(Culture Conditions)
5% $CO_2$ atmosphere at 37° C.
(Observation)

At day 3 and day 7, the cultured cells were observed with IN Cell Analyzer 2000 (trade name, manufactured by GE healthcare Bio-Sciences Corp.), and images thereof were acquired. Micrographs obtained are illustrated in FIG. 17.

Figure 17:
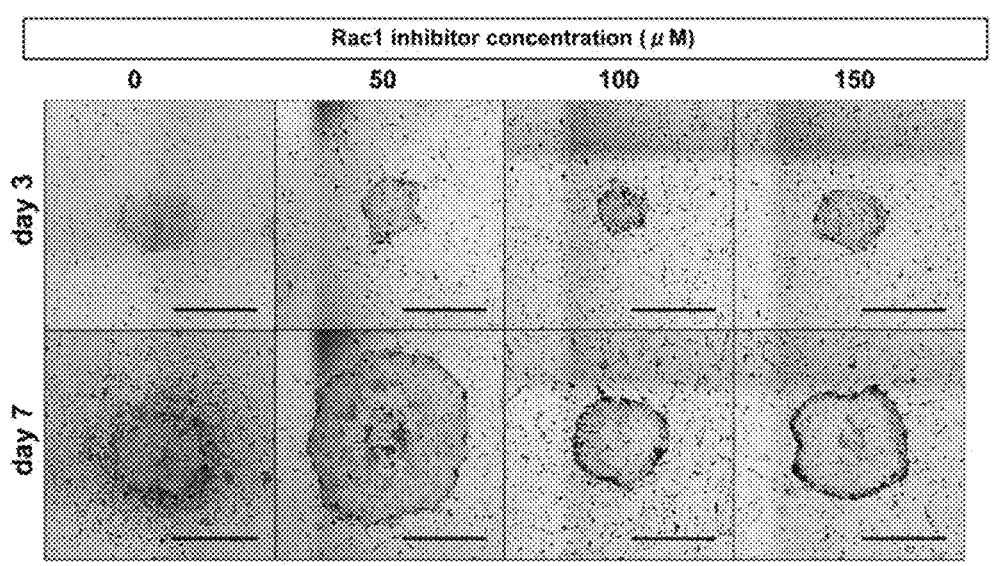
FIG. 17 illustrates exemplary micrographs taken when stem cells having pluripotency were cultured using MEF feeder cells.

As illustrated in FIG. 17, deviated cells grew in an outer edge part (outside) of a colony.

Next, cells were cultured and observed in the same manners as those described above except that a Rac-1 inhibitor (trade name: NSC23766, Calbiochem brand), which is a migration inhibitor, was added at 50, 100, or 150 µM at three days after the start of the culture (day 3). The obtained micrographs are illustrated in FIG. 17.

(Rac-1 Inhibitor Preparing and Adding Method)

Dilution of Rac-1 inhibitor: the Rac-1 inhibitor was diluted by using a medium (Repro Stem) (final concentration: 50 or 100 µM).

Further, bFGF (trade name, manufactured by ReproCELL, Inc., final concentration 5 ng/ml) was added thereto, and the Rac-1 inhibitor thus diluted was added to iPS cells.

As illustrated in FIG. 17, the addition of the Rac-1 inhibitor caused deviated cells, which had emerged in the outer edge part of the colony in the case where the Rac-1 inhibitor was not added, to emerge in the center part of the colony. The inhibition of cell migration allowed the deviated cells to emerge in the center part of the colony. This indicates that the inhibition of cell migration allows deviated cells to emerge in the center part of a colony, and this makes it possible to remove the deviated cells.

Culture was performed by using SNL feeder cells as the feeder cells and adding the Rac-1 inhibitor (50 or 100 µM) at three days after the culture start (day 3). Deviated cells grew in the center part of a colony (date not shown), as is the case with the Rac-1 inhibitor was not added.

[Influences of Hemagglutinin (HA) on iPS Cells (Part 2)]

Influences of HA on the deviated cells induced by the Rac-1 inhibitor were confirmed. First of all, iPS cells were seeded on feeder cells (day 0), and the culture medium was exchanged with a maintenance medium every 24 hours. At three days after the start (day 3), the 100 µM Rac-1 inhibitor was added and incubation was carried out for 24 hours. After washed with PBS twice, the culture medium was exchanged with a maintenance medium (day 4). At five days after the start (day 5), HA-1 was added and incubation was carried out for 24 hours. After washed with PBS twice, the culture medium was exchanged with a maintenance medium (day 6). Thereafter, until 8 days later (day 8), the culture medium was exchanged with a maintenance medium every 24 hours. After the culture, the expression of Oct3/4 of the cultured cells was confirmed by immunocytostaining, and further, DAPI staining was performed. The used cells and media, as well as the culture conditions are as follows. The methods for preparing and adding the Rac-1 inhibitor and HA are as mentioned above.

(Cell)
iPS cells: Tic (Np 39)
Feeder cells: MEF
(Medium)
iPS cells: Repro Stem (trade name, manufactured by ReproCELL Inc.), 5 ng/mL bFGF (trade name, manufactured by ReproCELL Inc.)
Feeder cells: DMEM (10% IBS (Gibco brand), 1% HEPES (manufactured by SIGMA Corporation), 1% Penicillin-streptomycin (manufactured by NACALAI TESQUE))
(Container)
24-well plate (bottom area: 1.9 cm$^2$/well, medium amount: 0.4 mL/well) (Observation)

At day 3, day 4, day 5, day 6, and day 8, the cultured cells were observed with IN Cell Analyzer 2000 (trade name, manufactured by GE healthcare Bio-Sciences Corp.), and images thereof were acquired. Micrographs obtained are illustrated in FIG. 18.

Further, as control, cells were cultured and observed in the same manners as those described above except that HA-1 was not added. Micrographs obtained are illustrated in FIG. 18.

Figure 18:
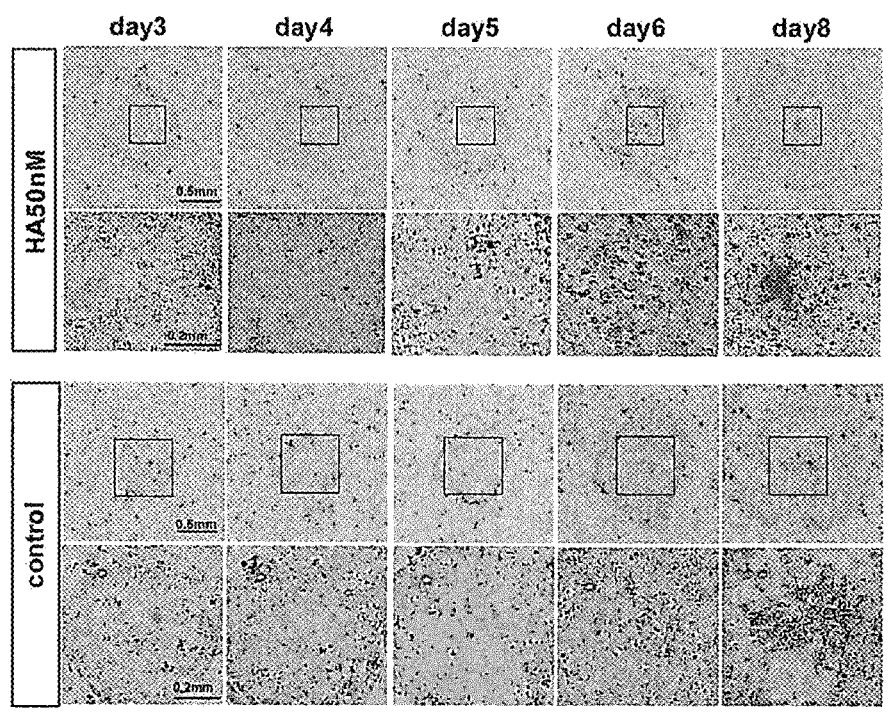
FIG. 18 illustrates exemplary micrographs in the case where a Rac-1 inhibitor was added at day 3, and thereafter, HA-1 having a final concentration of 50 nM was added at day 5.

As illustrated in FIG. 18, it is confirmed that the areas that included deviated cells that had emerged in the center part of the colony by addition of the Rac-1 inhibitor thereto shrank and/or disappeared due to addition of HA thereto.

[Influences of Feeder-Free Culture on iPS Cells]

Synthemax Surface (trade name, manufactured by Corning Inc.) was used as a culture surface, and iPS cells were seeded thereover. The culture medium was exchanged with a maintenance medium every 24 hours until day 7. After the culture, the expression of Oct3/4 of the cultured cells was confirmed by immunocytostaining, and DAPI staining was performed. The used cells and media, as well as the culture conditions are as follows.

(Cell)
iPS cells: Tic (Np 39)
(Medium)
mTeSR (Trade Mark) 1 medium (trade name, manufactured by STEMCELL, Technologies)
(Container)
24-well plate (bottom area: 1.9 cm$^2$/well, medium amount: 0.4 mL/well)
(Culture Conditions)
5% $CO_2$ atmosphere at 37° C.
(Observation)

At day 6, the cultured cells were observed with IN Cell Analyzer 2000 (trade name, manufactured by GE healthcare Bio-Sciences Corp.), and images thereof were acquired.

In the case of feeder-free culture, as is the case with the MEF feeder cells, deviated cells grew in the outer edge part (outside) of the colony.

Figure 19:
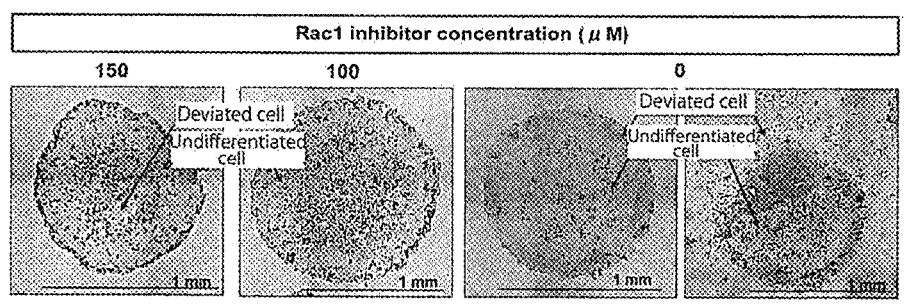
FIG. 19 illustrates exemplary micrographs of stem cells having pluripotency in feeder-free culture.

Next, cells were cultured and observed in the same manner as those described above except that the Rac-1 inhibitor was added at 100 or 150 µM at three days after the start of the culture (day 3). Micrographs obtained are illustrated in FIG. 19. FIG. 19 illustrates micrographs obtained in the case where the Rac-1 inhibitor was 150 µM. As illustrated in FIG. 19, the addition of the Rac-1 inhibitor allowed deviated cells to emerge in the center part of a colony. This indicates that in the case of the feeder-free culture as well, the inhibition of cell migration allows deviated cells to emerge in the center part of a colony, and this makes it possible to remove the deviated cells.

[Influences of Hemagglutinin (HA) on iPS Cells (Part 3)]

Cells were cultured and observed under the same conditions as those in the case of influences of hemagglutinin (HA) on iPS cells (part 1) except that cells 1 or 2 shown below were used as the cells, HA-1 was used as the HA, and the added concentration of HA was set to 50 nM. Micrographs obtained are illustrated in FIG. 20.

(Cell 1)
(Cell)
iPS cells: 201B7 strain
Feeder cells: SNL76/7 cells
(Medium)
iPS cells: Repro Stem (trade name, manufactured by ReproCELL Inc.)
Feeder cells: DMEM (7% FBS, 1% Penicillin-streptomycin solution)
(Cell 2)
(Cell)
iPS cells: 454E-2 strain
Feeder cells: SNL76/7 cells
(Medium)
iPS cells: Repro Stem (trade name, manufactured by ReproCELL Inc.)
Feeder cells: DMEM (7% FBS, 1% Penicillin-streptomycin solution)

Figure 20:
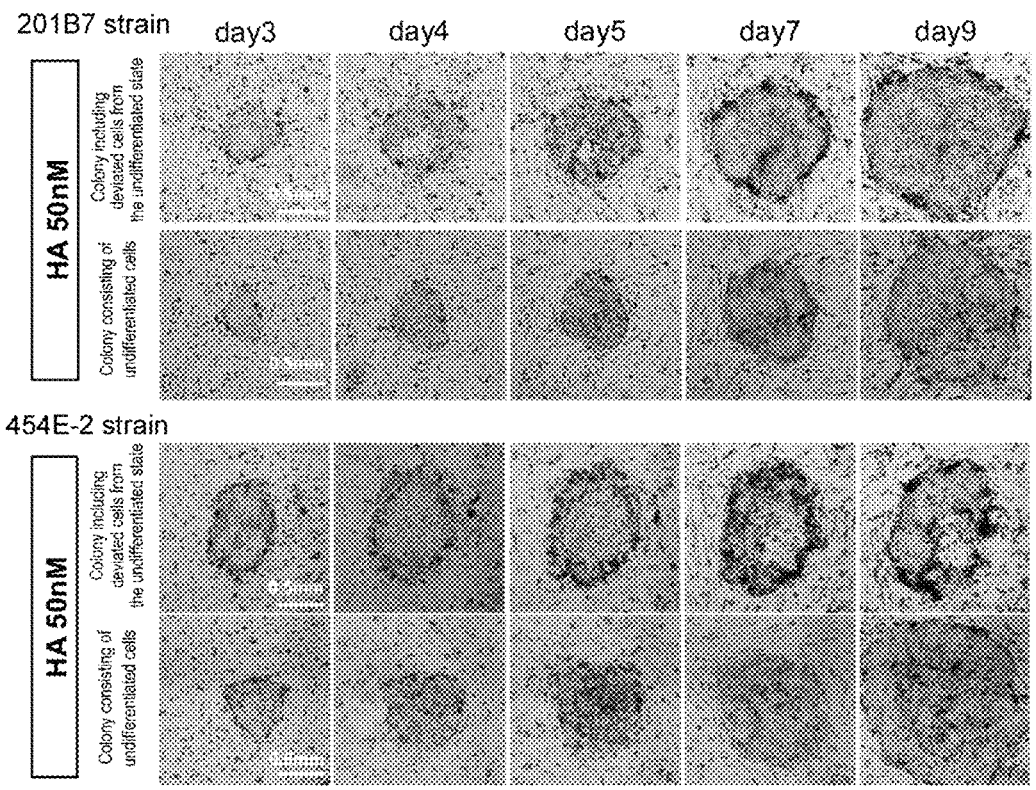
FIG. 20 illustrates exemplary micrographs in the case where a 201B7 strain or a 454E-2 strain was used.

As illustrated in FIG. 20, regarding a colony containing deviated cells, when HA was added, an area of deviated cells shrank and/or disappeared.

[Influences of Hemagglutinin (HA) on Subculture]

Figure 21:
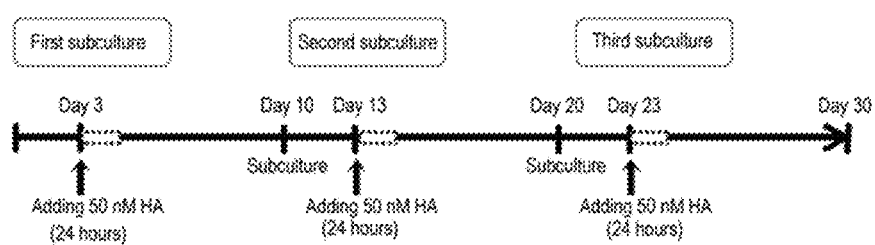
FIG. 21 explains a schedule of an experiment performed in Example.

According to the experiment schedule illustrated in FIG. 21, iPS cells were subcultured. First, iPS cells were seeded on feeder cells (day 0), and the culture medium was exchanged with a maintenance medium every 24 hours. At three days after the start (day 3), HA was added at 50 nM, and incubation was carried out for 24 hours. After washed with PBS twice, the culture medium was exchanged with a maintenance medium (day 4). Thereafter, until ten days after the start (day 10), the culture medium was exchanged with a maintenance medium every 24 hours. After the culture, subculture was carried out by normal operations, and at three days after the subculture (day 13), HA was added at 50 nM, and incubation was carried out for 24 hours. After washed with PBS twice, the culture medium was exchanged with a maintenance medium (day 14). Thereafter, ten-day culture, subculture, addition of HA and culture (10 days) were carried out. The expression of Oct3/4 of the cultured cells was confirmed by immunocytostaining, and further, DAPI staining was performed. The used cells and media, as well as culture conditions are as follows. As HA, HA-1 was used.

(Cell)
iPS cells: Tic (Np 39)
Feeder cells: SNL 76/7 (Np 5) treated with mitomycin C
(Medium)
iPS cells: Repro Stem (trade name, manufactured by Repro-CELL Inc.), 5 ng/mL FGF-2
Feeder cells: DMEM (7% FBS, 1% Penicillin-streptomycin solution)
(Container)
24-well plate (bottom area: 1.9 cm$^2$/well, medium amount: 0.4 mL/well)
(HA Preparing and Adding Method)
Dilution of HA: In order to make PBS included in the same dilution series have the same concentrations, two-stage dilution was performed. First, HA was serially diluted with PBS, and it was further diluted using a medium (Repro Stem). (The final concentration: 50 nM) Further, bFGF (final concentration: 5 ng/ml) was added, and the HA thus diluted was added to the iPS cells.
(Culture Conditions)
5% $CO_2$ atmosphere at 37° C.

After the subculture of iPS cells, in the exchange of the culture medium at t=72 h (day 3), HAs were added at respective concentrations, which was followed by the culture for 24 hours. Thereafter, in the exchange of the culture medium at t=96 h (day 4), the medium was switched to a HA-free medium, and the culture was continued.

(Observation)
At day 3, day 4, day 10, day 13, day 14, day 20, day 23, day 24 and day 30, the cultured cells were observed with IN Cell Analyzer 2000 (trade name, manufactured by GE healthcare Bio-Sciences Corp.), and images were acquired. Further, the numbers of formed colonies and undifferentiated colonies (colonies formed with undifferentiated cells, containing no deviated cells) were measured, and the ratio of undifferentiated colonies was calculated. The results are shown in FIG. 22.

As a comparative example, subculture was performed in the same conditions except that HA was not added. The results are shown in FIG. 22.

Figure 22:
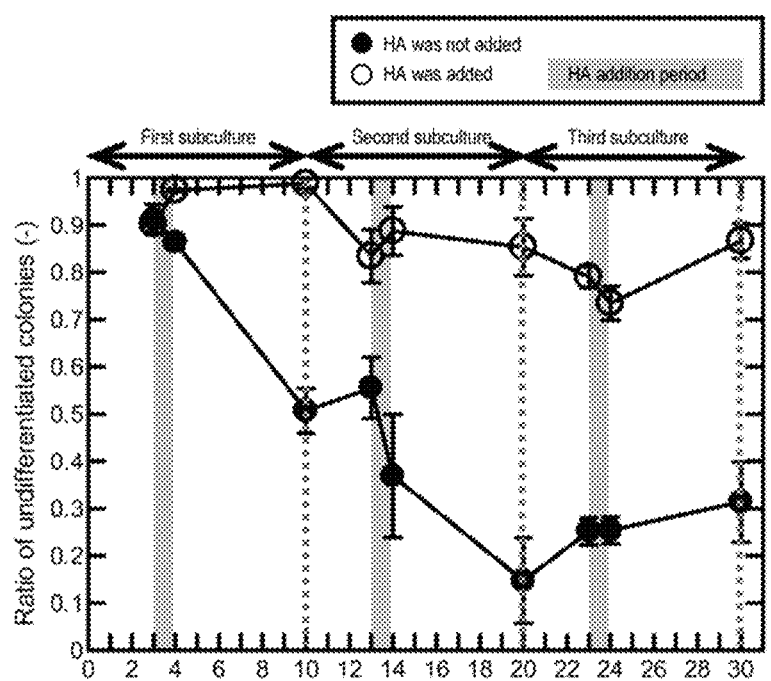
FIG. 22 is a graph showing ratios of undifferentiated colonies upon subculture.

In FIG. 22, white circles indicate a line of cultures in which HA was added, and black circles indicate a line of cultures in which HA was not added. As shown in FIG. 22, in the case where HA was added, as compared with the case where HA was not added, the ratio of undifferentiated colonies formed after subculture increased. In other words, by removing deviated cells, undifferentiated colonies were formed efficiently.

The invention claimed is:

1. A method of culturing undifferentiated stem cells having pluripotency, the method comprising:
   seeding stem cells having pluripotency on a surface to prepare a seeded stem cell culture,
   adding to the seeded stem cell culture an effective amount of a substance comprising hemagglutinin (HA) of a neurotoxin complex of *Clostridium botulinum* to prepare an undifferentiated stem cell culture, and
   subculturing the undifferentiated stem cells from the undifferentiated stem cell culture.

2. The method according to claim 1, wherein the stem cells having pluripotency are human pluripotent stem cells.

3. The method according to claim 2, wherein
   the human pluripotent stem cells are either human induced pluripotent stem (iPS) cells or human embryonic stem (ES) cells.

4. The method according to claim 1, wherein the substance further has an ability to bind to a cell surface.

5. The method according to claim 1, wherein the substance comprises a complex consisting of two or three components selected from the group consisting of three hemagglutinin subcomponents HA1, HA2, and HA3 of the neurotoxin complex of *Clostridium botulinum*.

6. The method according to claim 5, wherein the subcomponent HA3 of the complex is of *Clostridium botulinum* type A or *Clostridium botulinum* type B.

7. The method according to claim 1, wherein the seeded stem cell culture is a subculture.

8. The method according to claim 1, wherein the stem cells are seeded and cultured for at least 3 days prior to the adding of the substance.

9. The method according to claim 1, wherein the stem cells having pluripotency are iPS cells.

10. The method according to claim 1, wherein the seeded stem cell culture comprises at least one cell deviated from an undifferentiated state.

11. A method of culturing undifferentiated stem cells having pluripotency, the method comprising:
    adding to a seeded stem cell culture an effective amount of a substance that inhibits epithelial cadherin (E-cadherin) function to prepare an undifferentiated stem cell culture, and
    subculturing the undifferentiated stem cells having pluripotency from the undifferentiated stem cell culture wherein the substance comprises hemagglutinin (HA) of neurotoxin complex of *Clostridium botulinum*.

12. A method of culturing undifferentiated human stem cells having pluripotency, the method comprising:
    seeding human stem cells having pluripotency on a surface to prepare a seeded stem cell culture,
    adding to the seeded stem cell culture an effective amount of a substance that inhibits cell-cell adhesion to prepare an undifferentiated stem cell culture, and
    subculturing the undifferentiated human stem cells from the undifferentiated stem cell culture wherein the substance comprises hemagglutinin (HA) of neurotoxin complex of *Clostridium botulinum*.

13. The method according to claim 12, wherein the human stem cells having pluripotency are human iPS cells.

14. The method according to claim 12, wherein the substance comprises a complex consisting of two or three components selected from the group consisting of three hemagglutinin subcomponents HA1, HA2, and HA3 of the neurotoxin complex of *Clostridium botulinum*.

15. The method according to claim 14, wherein the subcomponent HA3 of the complex is of *Clostridium botulinum* type A or *Clostridium botulinum* type B.

16. The method according to claim 12, wherein the seeded stem cell culture comprises at least one cell deviated from an undifferentiated state.

17. A method of culturing undifferentiated iPS cells having pluripotency, the method comprising:

seeding iPS cells having pluripotency on a surface to prepare a seeded iPS cell culture, wherein the seeded iPS cell culture comprises at least one cell deviated from an undifferentiated state, and adding to the seeded iPS cell culture an effective amount of a substance that inhibits epithelial cadherin (E-cadherin) function wherein the substance comprises hemagglutinin (HA) of neurotoxin complex of *Clostridium botulinum*.

* * * * *